United States Patent [19]
Lewis et al.

[11] Patent Number: 5,170,661
[45] Date of Patent: Dec. 15, 1992

[54] APPARATUS FOR MONITORING FOULING IN AN ETHYLENE PLANT OIL QUENCH TOWER

[75] Inventors: Vincent E. Lewis, Missouri City; David J. Ciarella, Richmond; David G. Comer; Robert D. McClain, both of Sugar Land, all of Tex.

[73] Assignee: Nalco Chemical Company, Naperville, Ill.

[21] Appl. No.: 811,181

[22] Filed: Dec. 20, 1991

[51] Int. Cl.$^5$ .................... G01N 5/00; G01D 21/00
[52] U.S. Cl. ............................ 73/61.62; 73/866.5; 422/53; 436/6
[58] Field of Search .............. 73/61.62, 28.01, 61.41, 73/61.65, 61.63, 866.5, 863.86, 863.81, 86; 422/53; 436/6

[56] References Cited

U.S. PATENT DOCUMENTS

| | | | |
|---|---|---|---|
| 1,769,463 | 7/1930 | Rice | 422/53 |
| 3,080,747 | 3/1963 | Kerst | 73/61.62 |
| 3,649,187 | 3/1972 | Fisher | 422/53 |
| 3,861,876 | 1/1975 | Robertson et al. | 73/86 |
| 4,142,402 | 3/1979 | Mattioli et al. | 73/61.62 |
| 4,697,465 | 10/1987 | Evans et al. | 73/86 |

Primary Examiner—John E. Chapman
Assistant Examiner—Michael Brock
Attorney, Agent, or Firm—Robert A. Miller; Joseph B. Barrett

[57] ABSTRACT

Generally, the invention provides a fouling probe apparatus. The fouling probe including a heat transfer conduit having a first portion formed as a loop which is removably attached to a second portion which extends linearly. A hollow housing encases the apparatus. The housing has an open forward portion and an open rear portion. The open forward portion is attachable to an oil quench tower about an opening in the quench tower and the open rear portion is adapted to be securely attached to the linearly extending second portion of the heat transfer conduit. A fouling grid is attached to the first portion of the heat transfer conduit. The fouling grid is super-heated to accelerate fouling.

2 Claims, 2 Drawing Sheets

APPARATUS FOR MONITORING FOULING IN AN ETHYLENE PLANT OIL QUENCH TOWER

Background of the Invention

In an ethylene plant, hydrcarbons are heated at 800° C., in a furnace, in the presence of steam. This process is called cracking, and the principle product is ethylene. However, it is not the only compound produced. Other higher molecular weight hydrocarbons are also produced. The furnace effluent is cooled and compressed prior to separation, into its component hydrocarbons, by distillation.

Initial cooling is carried out in one of two ways. Depending on the furnace feedstock, either an oil quench tower and/or a water quench tower are used. If a heavier feedstock, such as naphtha, is used, both oil and water quench towers are used. However, if lighter feedstocks are used, such as ethane or propane, then only a water quench tower is needed. This is primarily true because much heavier side products are produced when naphtha is used as the feedstock. The heavier side products condense readily and become part of the oil quench stream, while the cooled gasses proceed through the water quench tower and on to compression.

Fouling in oil quench towers occurs when conjugated dienes, such as butadiene, isoprene, or styrene, start to polymerize due to heat from the tower. As the polymer grows, it becomes insoluble in the hydrocarbon stream and falls out of solution. This polymer then coats tower trays and other surfaces inhibiting heat transfer. It then takes more energy to provide the same work that would be possible if fouling did not take place. If fouling becomes severe enough, the unit may have to be shut down to clean up this tower. Thus, fouling costs ethylene producers money.

SUMMARY OF THE INVENTION

Generally, the invention provides a fouling probe apparatus. The fouling probe including a heat transfer conduit having a first portion formed as a loop which is removably attached to a second portion which extends linearly. A hollow housing encases the apparatus. The housing has an open forward portion and an open rear portion. The open forward portion is attachable to an oil quench tower about an opening in the quench tower and the open rear portion is adapted to be securely attached to the linearly extending second portion of the heat transfer conduit. A fouling grid is attached to the first portion of the heat transfer conduit. The fouling grid is super-heated to accelerate fouling.

According to a preferred embodiment, the fouling probe includes a hollow housing member having a front portion capable of attaching to an oil quench tower and sealing about an aperture in the oil quench tower. A heat transfer conduit having a first portion and second portion passes through and attaches to the housing. The second portion extends linearly and is removably attached to the first portion which is, preferably, loop-shaped. The conduit is capable of being heated to a temperature of greater than the interior of the quench tower. This enables an operation to perform accelerated fouling studies. A fouling grid is affixed to the first portion of the conduit which is located at a distal end of the conduit. The fouling grid is constructed from a plurality of interwoven metal wires. In operation, the conduit is inserted into and affixed to the housing such that the first portion of the conduit which is affixed to the fouling grid is capable of being introduced into the quench tower when the forward portion of the housing is affixed about the aperture of the quench tower.

DESCRIPTION OF THE PREFERRED EMBODIMENTS

The invention provides a fouling probe. The fouling probe is preferably used in an oil quench tower of an ethylene unit. The probe itself consists of a hollow piping or conduit (see FIG. 1) supporting at one end a metal grid. The grid is preferably constructed from interwoven metal wires and provides an environment for fouling materials to accumulate at an accelerate rate. Accordingly to one embodiment, the grid is made of carbon steel which is the same metallurgy as the trays in most oil quench towers. Since it is porous, the grid allows gases to pass through the probe, and this provides a large surface area onto which fouling materials can accumulate. The junction of the metal conduit and grid form a lip extending downwards at right angles to the grid (see FIG. 3). This provides a corner shape in which additional accelerated fouling can occur. The conduit is hollow to allow super-heated steam to circulate. This enables the probe to be heated to a temperature greater than that in the tower. The heat of the conduit is transferred to the grid. It is the heated grid which provides the mechanism of accelerating the fouling process.

Figure 1:
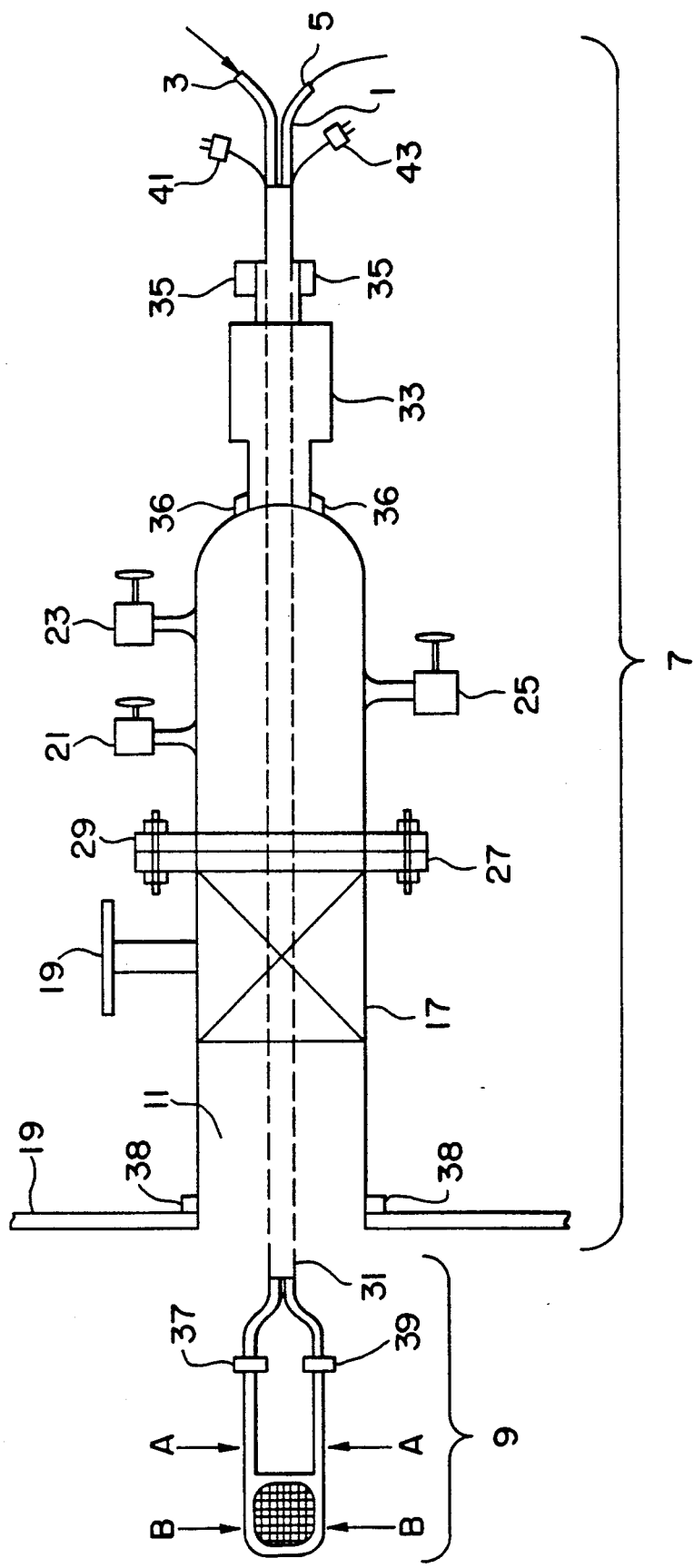
FIG. 1 is a cutaway view of the apparatus of the invention installed on an oil quench tower.

Referring to the figures, FIG. 1 shows a hollow conduit 1 through which super-heated pressurized steam is carried in a continuous circuit. In more detail, super-heated steam, preferably having a temperature of from 360°–400° F., enters the conduit 1 through inlet valve 3 and travels through the length of conduit 1 exiting via outlet valve 5. Conduit 1 is constructed from a linear extending section 7 which is removably attached to a looped probe tip section 9. The probe tip 9 is inserted into the tower via an aperture 11 in the tower 19.

Figure 2:
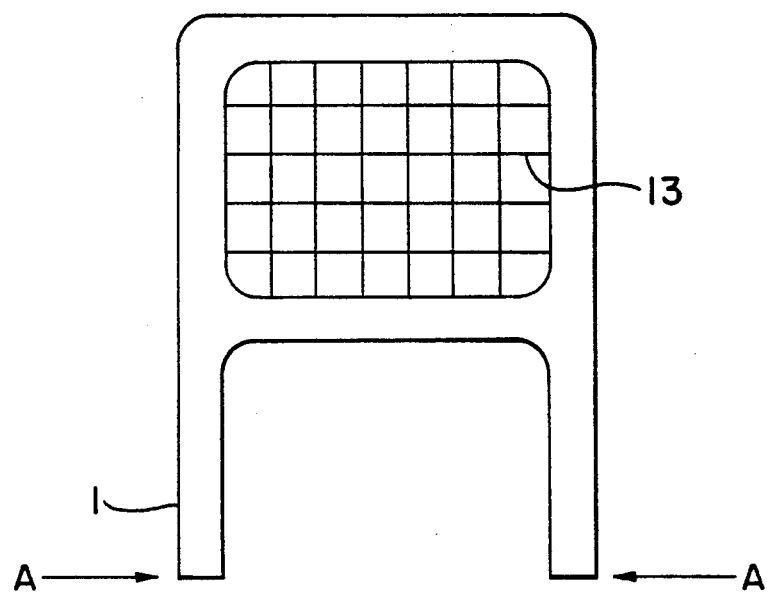
FIG. 2 is an expanded top view of the probe tip of the apparatus taken along line A—A of FIG. 1.
Figure 3:
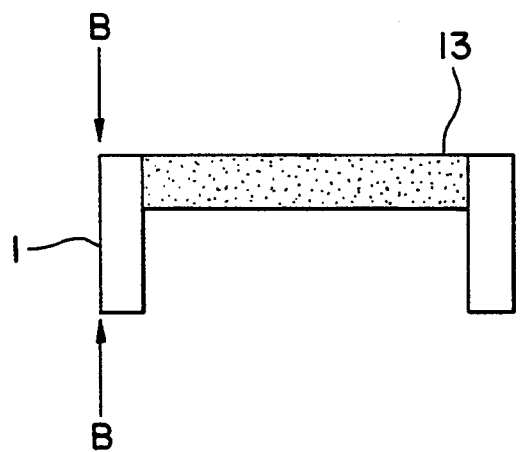
FIG. 3 is an expanded end view cross section taken along line B—B of FIG. 2 showing the junction between the grid and hollow conduit.

As shown in FIGS. 1, 2 and 3, the probe tip 9 is attached to an interwoven metal wire grid 13 which is securely connected between the parallel members of the conduit 1 which form the probe tip 9. The interwoven metal wires form a grid 13 onto which fouling materials will accumulate. Further, the grid 13 is heated to approximately the same temperature as the steam traveling in conduit 1 due to the transfer of heat from the conduit 1 to the wires forming the grid 13. Preferably, the wires which make up the grid 13 are the same metallurgy as the tower trays. In most cases, this metallurgy is carbon steel.

In more detail, as shown in FIG. 2, the probe tip 9 which is formed as a loop in one end of the conduit 1 completes a circuit through which super-heated pressurized steam travels, thus, heating the wires which form the grid 13. Onto this grid, fouling materials will accumulate and accelerated fouling studies can be performed.

Referring to the housing 17, shown in FIG. 1, the housing 17 is generally cylindrical in shape and includes a gate value 19 which, when closed, separates the environment of the tower 19 from the interior of the housing 17 when the probe is removed. The housing 17 also preferably includes several purge and pressure values 21, 23 and 25. According to one embodiment shown in FIG. 1, the housing 17 is constructed as two pieces which are joined together by bolts via flanges 27 and 29.

According to one embodiment shown in FIG. 1, the fouling probe includes a sleeve 31 which encircles the conduit 1 second portion. This sleeve is snugly attached to a packing gland 33 via fittings 35. The packing gland 33 is snugly attached to the housing 17 by fittings 36. In operation, the probe tip 9 is threaded through an opening in the rear of the housing (not shown). The packing gland 33 which surrounds the probe hermetically seals and attaches the probe via fittings 36 to the rear portion of housing 17. The housing 17 is then removably affixed over an aperture 11 in the side of the tower 19 via bolts or threads 38. The probe is constructed to be of sufficient length so that when the housing 17 is attached to the tower 19, the probe tip 9 resides in the interior of the tower.

According to one preferred embodiment shown in FIG. 1, the probe tip 9 includes thermal couples 37 and 39. The thermal couples 37 and 39 are electrically connected by wires 41 and 43 to a monitoring apparatus (not shown) which measures the external temperature of the conduit 1. Through this measurement, an operator can monitor and vary the temperature of the super-heated steam being introduced into conduit 1 in order to facilitate the accelerated fouling process of the apparatus of the invention.

The apparatus is used as generally described below. At regular intervals the probe is withdrawn and examined. To withdraw the probe it is pulled past the gate valve 19. The valve is closed and any liquid build-up in the housing is vented through the lower bleed valve 25 by means of a nitrogen purge through the top bleed valves 21 and 23. This allows safe removal of such toxic and/or carcinogenic species as benzene or styrene. The probe is then completely removed and the probe tip 9 taken off. Since the probe is inserted approximately 60 feet up on the tower, this allows for ease of handling in that a large probe does not have to be carried up and down the ladders on the tower. A new probe tip is placed on the probe and the used one is then weighed to give a measure of fouling.

This probe is intended to be placed in the vapor space between two trays where fouling is most prevalent. The inventors have discovered that in quench towers most fouling occurs on the underside of the trays, on the walls above the liquid level, and in corners or any other angular space, such as on the underside of trays. These locations indicate that fouling occurs in the vapor phase. The invention is, therefore, advantageously designed to allow vapor to pass through it while proving numerous angular spaces on which fouling can occur. The lip on the underside of the probe provides a further corner-like space in which fouling can more readily occur.

Since there is a known run length under known conditions, heating the probe above the tower operating temperature, gives an early indication of anticipated run length. For example, if heating the probe to 100° F. above the tower operating temperature provides 5 grams of foulant in 1 week, knowing that this corresponds to a two year run length allows for adjustment of the chemical treatment rate. Thus, if increasing the chemical treatment dosage decreases the amount of fouling to 1 gram in one week, then the run length of the tower should be correspondingly increased to a length greater than two years.

Changes can be made in the composition, operation and arrangement of the method of the present invention described herein without departing from the concept and scope of the invention as defined in the following claims:

We claim:
1. A fouling probe apparatus, comprising:
   a. a heat transfer conduit having a first portion formed as a loop removably attached to a second portion which extends linearly;
   b. a hollow housing having an open forward portion and an open rear portion, the open forward portion being attachable about an aperture in an oil quench tower, and the open rear portion being adapted to securely attach to the linearly extending second portion of the heat transfer conduit; and
   c. a wire metal grid attached to the heat transfer conduit first portion.

2. A fouling probe apparatus, comprising:
   a. a hollow housing member having a front open portion and an open rear portion, the open forward portion being adapted to attach and seal about an aperture in a surface of an oil quench tower, the rear open portion including attachment means;
   b. a hollow heat transfer conduit adapted to carry super-heated steam through its interior so that the conduit is heated to a temperature which is greater than the interior of the quench tower, the heat transfer conduit including a first portion formed as a loop removably attached to a linearly extending second portion, the heat transfer conduit being inserted into and removably attached to the housing member rear open portion attachment means; and
   c. a fouling grid affixed to the first portion of the conduit, said fouling grid constructed from a plurality of interwoven metal wires, whereby when said conduit is inserted into and attached to the housing open rear portion and when the forward open portion of the housing is attached about the aperture of the quench tower, the conduit first portion which is affixed to the fouling grid is introduced into the oil quench tower.

* * * * *